(12) United States Patent
    Pintor

(10) Patent No.: US 12,575,930 B2
(45) Date of Patent: Mar. 17, 2026

(54) HEART VALVE DEPLOYMENT AID

(71) Applicant: Edwards Lifesciences Corporation, Irvine, CA (US)

(72) Inventor: Rafael Pintor, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1079 days.

(21) Appl. No.: 17/649,971

(22) Filed: Feb. 4, 2022

(65) Prior Publication Data

US 2022/0151779 A1 May 19, 2022

Related U.S. Application Data

(63) Continuation of application No. PCT/US2020/043126, filed on Jul. 22, 2020.

(Continued)

(51) Int. Cl.
    *A61F 2/24* (2006.01)

(52) U.S. Cl.
    CPC .......... *A61F 2/2427* (2013.01); *A61F 2/2418* (2013.01)

(58) Field of Classification Search
    CPC ...... A61F 2/0095; A61F 2/2427; A61F 2/243; A61F 2/2433; A61F 2/2415;

(Continued)

(56) References Cited

U.S. PATENT DOCUMENTS 3,143,742 A    8/1964  Cromie
3,320,972 A    5/1967  High et al.

(Continued)

FOREIGN PATENT DOCUMENTS

EP    0125393 A1   11/1984
EP    0143246 A2   6/1985

(Continued)

OTHER PUBLICATIONS

Krakow, "3F Therapeutics, Inc. Announces the First Clinical Implantation of the 3F Enable Aortic Heart Valve.TM., a Patented, Sutureless Implantation, Replacement Heart Valve Intended to Save Valuable Surgery Time and Reduce Time RelatedComplications . . . " Healthcare Sales & Marketing Network News Feed, Jan. 18, 2005, pp. 1-2.

(Continued)

*Primary Examiner* — Sarah W Aleman
(74) *Attorney, Agent, or Firm* — Guy Cumberbatch

(57) ABSTRACT

Methods of implanting a hybrid prosthetic aortic heart valve having a valve member and a generally tubular plastically-expandable anchoring skirt attached to and projecting in an inflow direction therefrom. The anchoring skirt has an inflow end with an initial tapered shape with a lower (inflow/leading) end defining a smaller orifice. For implant, the heart valve is advanced with the anchoring skirt at the leading end, and ultimately a balloon catheter expands within the anchoring skirt to force it into contact with a subvalvular aspect of the aortic valve annulus. To facilitate advancement of the heart valve, the anchoring skirt is further crimped after removal from a storage container such as a jar. The crimping is done after removal from the storage container to preserve an initial manufactured orifice diameter at inflow/leading end of the anchoring skirt for passage of a delivery adapter used in the delivery process.

22 Claims, 10 Drawing Sheets

Related U.S. Application Data

(60) Provisional application No. 62/883,013, filed on Aug. 5, 2019.

(58) Field of Classification Search
CPC .... A61F 2/9522; A61F 2/9524; A61F 2/9525; A61F 2/9526
See application file for complete search history.

(56) References Cited

U.S. PATENT DOCUMENTS

| | | |
|---|---|---|
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,264,611 B1 | 7/2001 | Ishikawa et al. |
| 6,322,526 B1 | 11/2001 | Rosenman et al. |
| 6,350,282 B1 | 2/2002 | Eberhardt |
| 6,491,624 B1 | 12/2002 | Lotfi |
| 6,773,457 B2 | 8/2004 | Ivancev et al. |
| 7,037,333 B2 | 5/2006 | Myers et al. |
| 7,998,151 B2 | 8/2011 | St. Goar et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |

(56) References Cited

U.S. PATENT DOCUMENTS

| | | |
|---|---|---|
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244546 A1 | 10/2007 | Francis |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |

(56)　　　　　References Cited

U.S. PATENT DOCUMENTS

| | | |
|---|---|---|
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0033543 A1 | 2/2008 | Gurskis et al. |
| 2008/0065198 A1 | 3/2008 | Quintessenza |
| 2008/0119875 A1 | 5/2008 | Ino et al. |
| 2008/0154356 A1 | 6/2008 | Obermiller et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0249894 A1 | 9/2010 | Oba et al. |
| 2010/0249908 A1 | 9/2010 | Chau et al. |
| 2010/0331972 A1 | 12/2010 | Pintor et al. |
| 2011/0022165 A1 | 1/2011 | Oba et al. |
| 2011/0040372 A1 | 2/2011 | Hansen et al. |
| 2011/0147251 A1 | 6/2011 | Hodshon et al. |
| 2012/0065729 A1* | 3/2012 | Pintor .................. A61F 2/2418 |
| | | 623/2.14 |
| 2012/0101569 A1* | 4/2012 | Mearns ................. A61F 2/2427 |
| | | 623/2.1 |
| 2012/0141656 A1 | 6/2012 | Orr et al. |
| 2012/0150288 A1 | 6/2012 | Hodshon et al. |
| 2013/0053949 A1 | 2/2013 | Pintor et al. |
| 2013/0116777 A1 | 5/2013 | Pintor et al. |
| 2014/0058194 A1 | 2/2014 | Soletti et al. |
| 2014/0079758 A1 | 3/2014 | Hall et al. |
| 2014/0144000 A1 | 5/2014 | Creaven et al. |

FOREIGN PATENT DOCUMENTS

| | | |
|---|---|---|
| EP | 2921135 A1 | 9/2015 |
| SU | 1116573 A1 | 7/1985 |
| SU | 1697790 A1 | 12/1991 |
| WO | 9213502 A1 | 8/1992 |
| WO | 9742871 A1 | 11/1997 |
| WO | 2007146261 A2 | 12/2007 |
| WO | WO-2014164832 A1 | 10/2014 |

OTHER PUBLICATIONS

Sadowski, Jerzy; Kapelak, Boguslaw; Bartus, Krzysztof, "Suture-less Heart Valve Implantation—A Case Study," Touch Briefings, 2005, pp. 48-50.

* cited by examiner

HEART VALVE DEPLOYMENT AID

CROSS REFERENCE TO RELATED APPLICATIONS

This application is a continuation of International Patent Application No. PCT/US20/43126, filed Jul. 22, 2020, which claims the benefit of U.S. Patent Application No. 62/883,013, filed Aug. 5, 2019, the entire contents all of which are incorporated for all purposes.

TECHNICAL FIELD

The present disclosure generally relates to an aid for use when implanting prosthetic heart valves and, more particularly, to an aid which adjusts a delivery profile of a prosthetic heart valve.

BACKGROUND

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually, and about one-half of these patients received mechanical heart valves, which are composed of rigid, synthetic materials. The remaining patients received bioprosthetic heart valve replacements, which utilize biologically derived tissues for flexible fluid occluding leaflets.

The most successful bioprosthetic materials for flexible leaflets are whole porcine valves and separate leaflets made from bovine pericardium stitched together to form a tri-leaflet valve. However, flexible leaflets formed of polymeric, fiber-reinforced, and other synthetic materials have also been proposed. The most common flexible leaflet valve construction includes three leaflets mounted to commissure posts around a peripheral non-expandable support structure with free edges that project toward an outflow direction and meet or coapt in the middle of the flowstream. A suture-permeable sewing ring is provided around the inflow end.

One prior bioprosthetic valve for aortic valve replacement is provided by the Edwards Intuity® valve system available from Edwards Lifesciences of Irvine, CA. Aspects of the Edwards Intuity valve system are disclosed in U.S. Pat. Nos. 8,641,757 and 9,370,418 both to Pintor, et al. and U.S. Pat. No. 8,869,982 to Hodshon, et al. The Edwards Intuity valve is a hybrid of a generally non-expandable valve member and an expandable anchoring stent that helps secure the valve in place in a shorter amount of time. The implant process only requires three sutures, which reduces the time-consuming process of tying knots. A delivery system advances the Edwards Intuity valve with the stent at the leading end until it is located within the left ventricle, at which point a balloon inflates to expand the stent against the ventricular wall. The long handle and delivery system design facilitate access through smaller incisions (mini-sternotomy or right anterior thoracotomy) than used in full sternotomies.

Although the anchoring stent on the Intuity valve is conically crimped down on its inflow (leading) end, sometimes the overall diameter is larger than desired and the surgeon has difficulty implanting the valve. This situation can arise, for example, when the valve sizer used to assess the native valve orifice does not accurately reflect the size and geometry of the Intuity valve. Difficulties can also be experienced by aggressive surgeons that force the largest diameter sizer they can into the valve annulus/LVOT to determine the valve size to be implanted. For example, challenges include difficulty seating the valve, valve pop up, valve displacement while tying implant sutures, or improper valve position after tying the sutures.

In view of the foregoing, it is apparent that there is a need in the art for a solution to problems associated with sizing and delivery of hybrid prosthetic heart valves.

SUMMARY

The present application provides methods of implanting a hybrid prosthetic aortic heart valve having a valve member and a generally tubular plastically-expandable anchoring skirt attached to and projecting in an inflow direction therefrom. The anchoring skirt has an inflow end with an initial tapered shape with a lower (inflow/leading) end defining a smaller orifice. For implant, the heart valve is advanced with the anchoring skirt at the leading end, and ultimately a balloon catheter expands within the anchoring skirt to force it into contact with a subvalvular aspect of the aortic valve annulus. To facilitate advancement of the heart valve, the anchoring skirt is further crimped after removal from a storage container such as a jar. The crimping is done after removal from the storage container to preserve an initial manufactured orifice diameter at inflow/leading end of the anchoring skirt for passage of a delivery adapter used in the delivery process.

An exemplary method comprises first procuring a hybrid prosthetic aortic heart valve having a valve member and a generally tubular plastically-expandable anchoring skirt attached to and projecting in an inflow direction from the valve member. The anchoring skirt has an initial shape that decreases in radial dimension from an outflow end defining a first diameter orifice and connected to the valve member to an inflow end having a second diameter orifice. The heart valve is attached to a valve holder projecting in an outflow direction. A user passes a parting sleeve through the anchoring skirt and valve member and attaches the parting sleeve to the valve holder. The user then advances the anchoring skirt into a crimping die to crimp the inflow end of the anchoring skirt so that the second diameter orifice is smaller than the first diameter orifice. The heart valve is delivered anchoring skirt first to an aortic heart valve annulus; and the anchoring skirt plastically-expanded to contact the aortic heart valve annulus.

In the exemplary method, the crimping die preferably comprises a body with a throughbore along a longitudinal axis and an enlarged crimping cavity opening at a first longitudinal end of the body, the method including pushing the heart valve anchoring skirt first into the crimping cavity. In one embodiment, the heart valve has a sealing ring surrounding a junction between the valve member and anchoring skirt, and the method includes pushing the heart valve anchoring skirt first into the crimping cavity until the sealing ring contacts the first longitudinal end of the body. The sealing ring may have an axially undulating shape with peaks and valleys, and the first longitudinal end of the body has a matching axially undulating shape surrounding the crimping cavity. Preferably, the crimping die body has an external shape that inhibits the body from rolling around the longitudinal axis on a support surface.

The initial shape of the anchoring skirt may be conical, and the crimping cavity is hemispherical to crimp the inflow end of the anchoring skirt into a spherical curvature. Alternatively, the initial shape of the anchoring skirt is generally conical with a trilobular crimped inflow end, and the crimping cavity is generally hemispherical with a trilobular contour that matches the shape of the anchoring skirt so as to crimp the inflow end of the anchoring skirt into a spherical curvature.

The step of passing the parting sleeve through the anchoring skirt and valve member and attaching the parting sleeve to the valve holder desirably occurs before the heart valve is removed from a storage jar, and the method further includes attaching a handling shaft to the parting sleeve to remove the heart valve from the storage jar.

Another method of implanting a hybrid prosthetic aortic heart valve, comprises first procuring a hybrid prosthetic aortic heart valve having a valve member and a generally tubular plastically-expandable anchoring skirt attached to and projecting in an inflow direction from the valve member. The anchoring skirt has an outflow end defining a first diameter orifice and connected to the valve member and an inflow end having a second diameter orifice, and the heart valve is attached to a valve holder projecting in an outflow direction. The method comprises passing a parting sleeve through the anchoring skirt and valve member and attaching the parting sleeve to the valve holder. A user crimps the inflow end of the anchoring skirt so that the second diameter orifice is smaller than the first diameter orifice. The heart valve is delivered anchoring skirt first to an aortic heart valve annulus; and the anchoring skirt plastically-expanded to contact the aortic heart valve annulus.

Another aspect of the present application is a kit including a hybrid prosthetic aortic heart valve and a crimping die. The hybrid prosthetic aortic heart valve has a valve member and a generally tubular plastically-expandable anchoring skirt attached to and projecting in an inflow direction from the valve member. The anchoring skirt has an initial shape that decreases in radial dimension from an outflow end defining a first diameter orifice and connected to the valve member to an inflow end having a second diameter orifice. The crimping die includes a crimping cavity, and is configured to crimp the inflow end of the anchoring skirt so that the second diameter orifice is smaller than the first diameter orifice when the valve is advanced anchoring-skirt first into the crimping cavity. In a preferred embodiment, the crimping die comprises a body with a throughbore along a longitudinal axis and the crimping cavity opens at a first longitudinal end of the body. Further, the heart valve may have a sealing ring surrounding a junction between the valve member and anchoring skirt such that the heart valve is advanced into the crimping cavity until the sealing ring contacts the first longitudinal end of the body. The sealing ring may have an axially undulating shape with peaks and valleys, and the first longitudinal end of the crimping die body has a matching axially undulating shape surrounding the crimping cavity. The crimping die body may have an external shape that inhibits the body from rolling around the longitudinal axis on a support surface.

All methods disclosed herein are also applicable as simulated methods, for example, for training, research, or education. For example, a method for treating a patient also encompasses simulating the method on a simulated patient or portion thereof. The simulated patent or portion thereof can be a whole or partial cadaver, a physical model, a virtual model (in silico), or a combination thereof, and can simulate a human or non-human patient.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIGS. 13A and 13B are elevational views of a hybrid prosthetic heart valve before and after compression of the expandable skirt using the crimping die;

FIGS. 14A and 14B are elevational views of just the expandable skirt before and after compression using the crimping die;

DETAILED DESCRIPTION OF CERTAIN EMBODIMENTS

As mentioned above, one promising prior art technique for heart valve replacement is a hybrid valve with a non-expandable valve member and an expandable stent thereon which, though still requiring cardiopulmonary bypass, can be implanted in a much shorter time frame. The hybrid valve is delivered through direct-access ports introduced through the chest.

Figure 1:
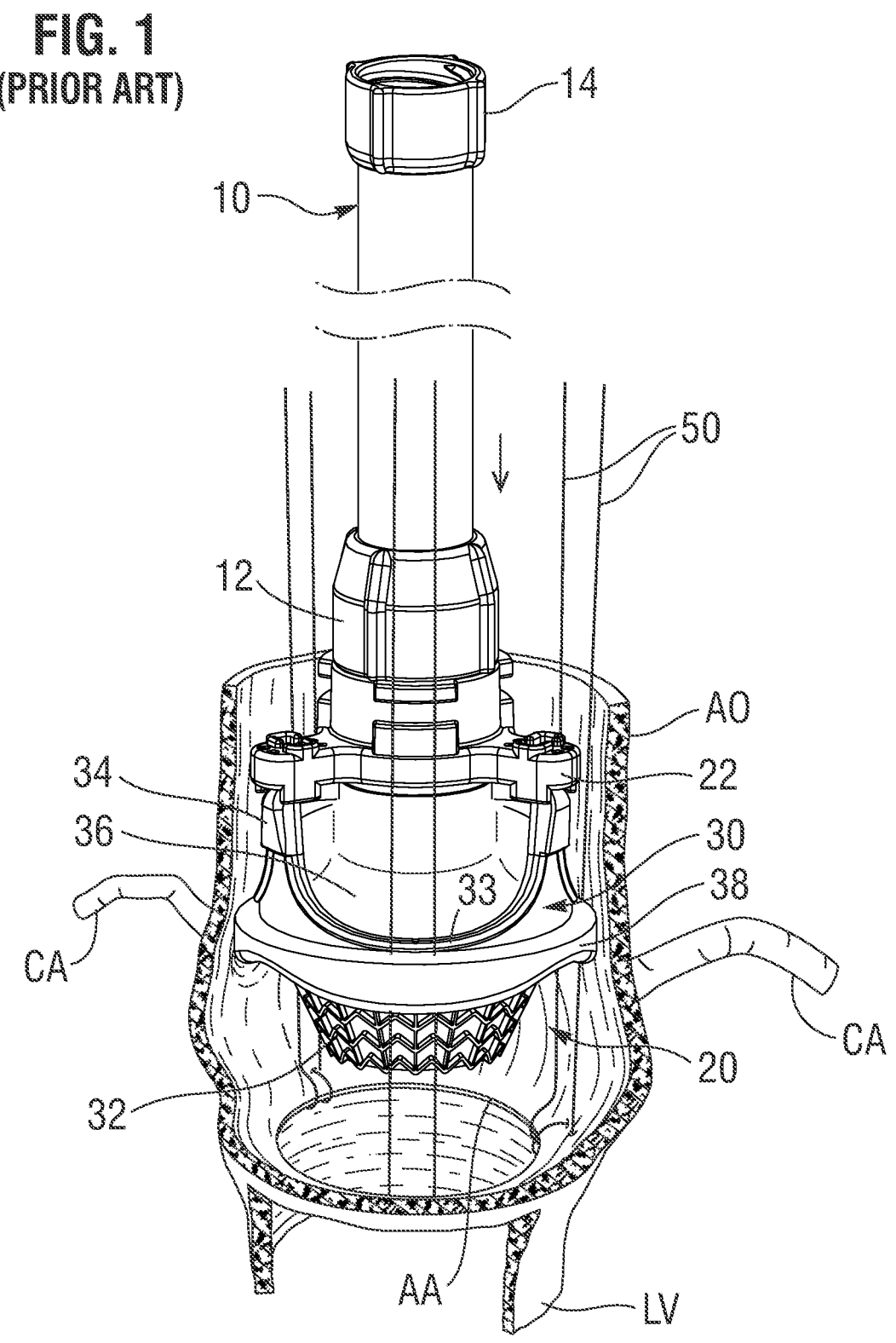
FIG. 1 illustrates delivery to an aortic annulus of a prior art heart valve/holder combination using a valve delivery tube.

FIG. 1 illustrates a snapshot in the process of delivering a prior art heart valve 20 to an aortic annulus AA using a valve delivery tube or handle 10. As will be seen, the valve delivery handle 10 has a distal coupler 12 and a proximal coupler 14. For purpose of orientation, the heart valve 20 has an inflow end down and an outflow end up, and the terms proximal and distal are defined from the perspective of the surgeon delivering the valve inflow end first. Thus, proximal is synonymous with up or outflow, and distal with down or inflow.

The illustrated prosthetic heart valve 20 is considered a hybrid type because it has a non-expandable, non-collapsible valve member 30 and an expandable anchoring skirt 32 attached to and projecting from a distal end of the valve member 30. The valve member 30 may take a variety of forms, but preferably includes a cloth-covered wireform that follows an undulating path around the periphery of the valve with alternating cusps 33 and commissure posts 34. A plurality of flexible leaflets 36 extend across a generally circular orifice defined within the valve member 30, each of which receives peripheral support along the wireform, in particular by two adjacent commissure posts 34. An annular, preferably contoured, sewing or sealing ring 38 circumscribes the valve 20 at an axial location approximately between the valve member 30 and expandable anchoring skirt 32.

The term "valve member" refers to that component of a heart valve that possesses the fluid occluding surfaces to prevent blood flow in one direction while permitting it in another. Various constructions of valve members are available, including those with flexible leaflets and those with rigid leaflets, or even a ball and cage arrangement. The leaflets may be bioprosthetic, synthetic, metallic, or other suitable expedients. When used for aortic valve replacement, the valve member 30 preferably has three flexible leaflets 36 which provide the fluid occluding surfaces to replace the function of the native valve leaflets. In various preferred embodiments, the valve leaflets may be taken from another human heart (cadaver), a cow (bovine), a pig (porcine valve) or a horse (equine). The three leaflets are supported by the internal wireform, which typically include a synthetic (metallic and/or polymeric) support structure of one or more components covered with cloth for ease of attachment of the leaflets.

Although the exemplary valve member 30 is constructed as mentioned, the present invention is broader and encompasses any valve member 30 having an expandable anchoring skirt 32 projecting from an inflow end thereof (for example, one without a wireform or even a mechanical valve member).

For definitional purposes, the terms "skirt" or "anchoring skirt" refer to an expandable structural component of a heart valve that is capable of attaching to tissue of a heart valve annulus. The anchoring skirt 32 described herein may be tubular, have varying shapes or diameters. Other anchoring skirts that could be used with valves of the present invention include rigid rings, spirally-wound tubes, and other such tubes that fit tightly within a valve annulus and define an orifice therethrough for the passage of blood.

By utilizing an expandable skirt 32 coupled to a non-expandable valve member 30, the duration of the implant operation is greatly reduced as compared with a conventional sewing procedure utilizing an array of sutures. The expandable skirt 32 may simply be radially expanded outward into contact with the implantation site, or may be provided with additional anchoring means, such as barbs. This provides a rapid connection means as it does not require the time-consuming process of suturing the valve to the annulus. The operation may be carried out using a conventional open-heart approach and cardiopulmonary bypass. In one advantageous feature, the time on bypass is greatly reduced due to the relative speed of implanting the expandable stent.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or dimensionally stable, merely that the valve member is not expandable/collapsible like some proposed minimally-invasively or percutaneously-delivered valves, and some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

In a particularly preferred embodiment, the prosthetic valve 20 comprises a commercially available, non-expandable prosthetic valve member 30, such as the Carpentier-Edwards PERIMOUNT Magna® Aortic Heart Valve available from Edwards Lifesciences, while the anchoring skirt 32 includes an inner plastically-expandable frame or stent covered with fabric. In another embodiment, the valve member 30 comprises a PERIMOUNT Magna® Aortic valve subjected to GLX tissue treatment, which allows for dry packaging and sterilization and eliminates the need to rinse the valves before implantation. In this sense, a "commercially available" prosthetic heart valve is an off-the-shelf (e.g., suitable for stand-alone sale and use) prosthetic heart valve defining therein a non-expandable, non-collapsible support structure and having a sealing ring capable of being implanted using sutures through the sealing ring in an open-heart, surgical procedure. In other examples, the prosthetic valve member is similar to or derived from, but is not identical to a commercially available device. In yet other examples, the prosthetic valve member is a specially designed device.

Figures 2, 2A, 2B:
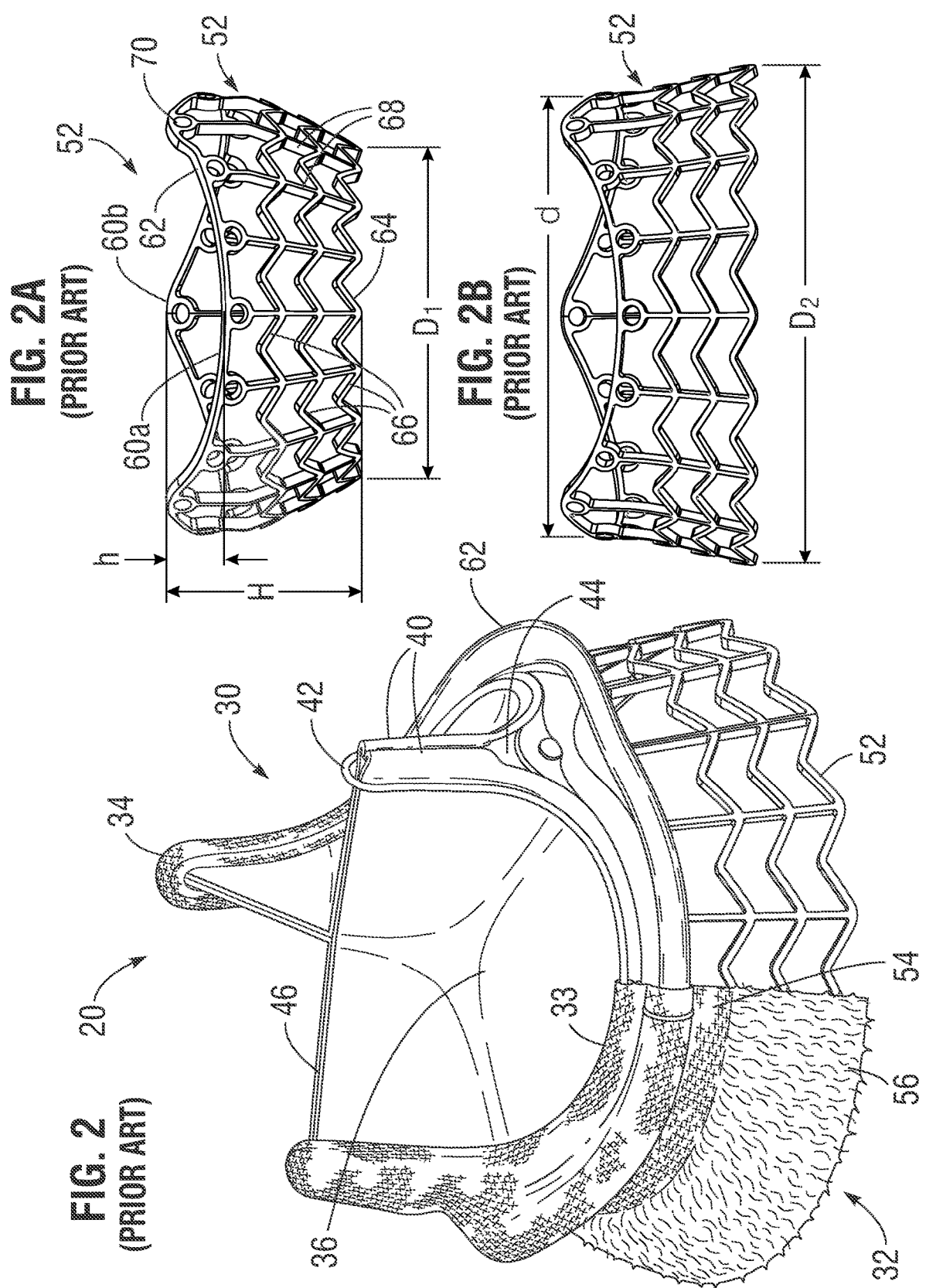
FIG. 2 is a partially cutaway perspective view of a prior art assembled hybrid prosthetic heart valve.
FIGS. 2A and 2B are elevational views of a prior art anchoring skirt shown in both radially contracted and expanded states, respectively.

In the cutaway portion of FIG. 2, each of the three leaflets 36 includes outwardly projecting tabs 40 that pass through inverted U-shaped commissure posts 42 of an undulating wireform and wrap around cloth-covered upstanding posts 44 of an inner polymer band. Tabs 40 from adjacent leaflets converge outside of the wireform commissure posts 42 and are sewn together to provide an outer anchor for leaflet free edges 46. In use, fluid forces close the leaflets (coaptation)

as seen in FIG. 2 and exert substantial force on the occluded valve, which translates into inward force on the leaflet free edges 46. The assembly of the wrapped leaflet tabs 40 and cloth-covered posts 44 sewn together provides a solid anchor that is prevented from inward movement by the metallic wireform posts 42. Some flexing is acceptable and even desirable.

One feature of the valve member 30 that is often utilized is the sewing or sealing ring 38 that surrounds the inflow end thereof. The sealing ring 38 conforms to an upper end of the anchoring skirt 32 and is located at the junction of the skirt and the valve member 30. Moreover, the sealing ring 38 presents an outward flange that contacts an outflow side of the part of annulus, while the anchoring skirt 32 expands and contacts the opposite, ventricular side of the annulus, therefore securing the heart valve 20 to the annulus from both sides. Furthermore, the presence of the sealing ring 38 provides an opportunity for the surgeon to use conventional sutures to secure the heart valve 20 to the annulus as a contingency.

The preferred sealing ring 38 defines a relatively planar upper or outflow face and an undulating lower face. Cusps 33 of the valve structure abut the sealing ring upper face opposite locations where the lower face defines peaks. Conversely, the valve commissure posts 34 align with locations where the sealing ring 38 lower face defines troughs. The undulating shape of the lower face advantageously matches the anatomical contours of the aortic side of the annulus AA, that is, the supra-annular shelf. The ring 38 preferably comprises a suture-permeable material such as rolled synthetic fabric or a silicone inner core covered by a synthetic fabric. In the latter case, the silicone may be molded to define the contour of the lower face and the fabric cover conforms thereover.

As seen in FIG. 2, the anchoring skirt 32 comprises an inner stent frame 52 assembled within a tubular section of fabric 54 which is then drawn taut around the stent frame, inside and out, and sewn thereto to form the cloth-covered skirt 32. A thicker, more plush fabric flange 56 may also be attached around the fabric 54 for additional sealing benefits. It should be noted that FIG. 2 shows the stent frame 52 in an outwardly expanded state, which occurs during implant as mentioned.

In an assembly process, the stent frame 52 may be initially tubular and then crimped to a conical shape as see in FIG. 2A, for example. Of course, the frame 52 may be crimped first and then covered with cloth. FIG. 2B shows the expanded stent frame 52 isolated and expanded into its implant shape.

With reference again to the implant step of FIG. 1, the aortic annulus AA is shown schematically isolated and it should be understood that various anatomical structures are not shown for clarity. The annulus AA includes a fibrous ring of tissue that projects inward from surrounding heart walls. The annulus AA defines an orifice between the ascending aorta AO and the left ventricle LV. Although not shown, native leaflets project inward at the annulus AA to form a one-way valve at the orifice. The leaflets may be removed prior to the procedure, or preferably left in place and outwardly compressed by the expandable anchoring skirt 32. If the leaflets are removed, some of the calcified annulus may also be removed, such as with a rongeur. The ascending aorta AO commences at the annulus AA with three outward bulges or sinuses, two of which are centered at coronary ostia (openings) leading to coronary arteries CA. It is important to orient the prosthetic valve 20 so that the commissure posts 34 are not aligned with and thus not blocking the coronary ostia.

FIG. 1 shows a plurality of pre-installed guide sutures 50. The surgeon attaches the guide sutures 50 at three evenly spaced locations around the aortic annulus AA. In the illustrated embodiment, the guide sutures 50 attach to locations below or corresponding to the nadirs of the native cusps (that is, two guide sutures are aligned with the coronary sinuses, and the third centered below the non-coronary sinus). The guide sutures 50 are preferably looped twice through the annulus AA from the outflow or ascending aorta side to the inflow or ventricular side. Of course, other suturing methods or pledgets may be used depending on surgeon preference.

The guide sutures 50 extend in pairs of free lengths from the annulus AA and out of the operating site. The prosthetic heart valve 20 mounts on the distal end of the delivery handle 10 and the surgeon advances the valve into position within the aortic annulus AA along the guide sutures 50. That is, the surgeon threads the three pairs of guide sutures 50 through evenly spaced locations around the suture-permeable ring 38. If the guide sutures 50, as illustrated, anchor to the annulus AA below the aortic sinuses, they thread through the ring 38 mid-way between the valve commissure posts 34, in particular at cusp regions 33 of the sealing ring that are axially thicker than the commissure locations.

FIG. 1 illustrates the dual nature of the valve delivery handle 10 in that it provides both a portion of the handle of the delivery system, as well as a through lumen that leads directly through the holder 22 and a leaflet parting member (described below) to the space within the anchoring skirt 32. Although not shown, other elements of the delivery system mate with the proximal coupler 14 to provide an elongated access channel for delivery of an expander such as a balloon to a space within the anchoring skirt 32.

The surgeon advances the heart valve 20 until it rests in a desired implant position at the aortic annulus AA. The undulating suture-permeable ring 38 desirably contacts the ascending aorta AO side of the annulus AA, and is thus said to be in a supra-annular position. Such a position enables selection of a larger orifice prosthetic valve 20 as opposed to placing the ring 38, which by definition surrounds the valve orifice, within the annulus AA, or infra-annularly. Further details of the delivery procedure are shown and described in U.S. Pat. No. 8,641,757, filed Jun. 23, 2011, the contents of which are expressly incorporated herein.

After seating the prosthetic heart valve 20 at the aortic annulus AA, the anchoring skirt 32 is expanded into contact with a subvalvular aspect of the aortic valve annulus, such as with a balloon, to anchor the valve 20 to the annulus AA and seal a concentric space between aortic annulus/LVOT and bio-prosthesis so as to prevent paravalvular leaks. The operator then severs any retention sutures (not shown) between the holder 22 and valve 20, deflates the balloon and withdraws it along with the entire assembly of the leaflet parting member, holder 22 and valve delivery handle 10. Finally, the guide sutures 50 will be tied off to further secure the valve in place.

The inner stent frame 52 seen in detail in FIGS. 2A and 2B may be similar to an expandable stainless steel stent used in the Edwards SAPIEN Transcatheter Heart Valve. However, the material is not limited to stainless steel, and other materials such as Co—Cr alloys, etc., may be used. In one embodiment, the radial thickness of the plurality of struts is around 0.4-0.6 mm In a preferred embodiment, the material used should have an elongation at break greater than 33%, and an ultimate tensile strength of greater than about 490 MPa. The stent frame 52 may be initially formed in several ways. For instance, a tubular portion of suitable metal such as stainless steel may be laser cut to length and to form the latticework of chevron-shaped interconnected struts. After laser cutting, the stent frame 52 is desirably electro-polished. Other methods including wire bending and the like are also possible. Following manufacture, the inner stent frame 52 assumes a crimped, tapered configuration that facilitates insertion through the calcified native aortic valve (see FIG. 1).

It should be noted that the stent frame 52 in FIG. 2A commences at its upper end in a generally tubular shape and then angles inwardly to be tapered toward its lower end. That is, the generally tubular portion has a height h which is only a portion of the total height H. As shown, the tubular portion has a height h which generally corresponds to the height between troughs 60a and the peaks 60b of an upper end 62 of the stent. The upper end 62 is preferably defined by a thicker wire for reinforcement. The upper end 62 follows an undulating path with alternating arcuate troughs 60a and pointed peaks 60b that generally corresponds to the undulating contour of the sewing ring 38 (see FIG. 3A). Desirably, the height h of the peaks 60b above the troughs 60a is between about 25-36% of the total stent height H, with the ratio gradually increasing for larger valve sizes. Because of the two different profiles, the diameter d of the lower end of the stent is somewhat larger than it would be if the stent were crimped to be completely conical.

Figures 3A, 4A, 4B, 5:
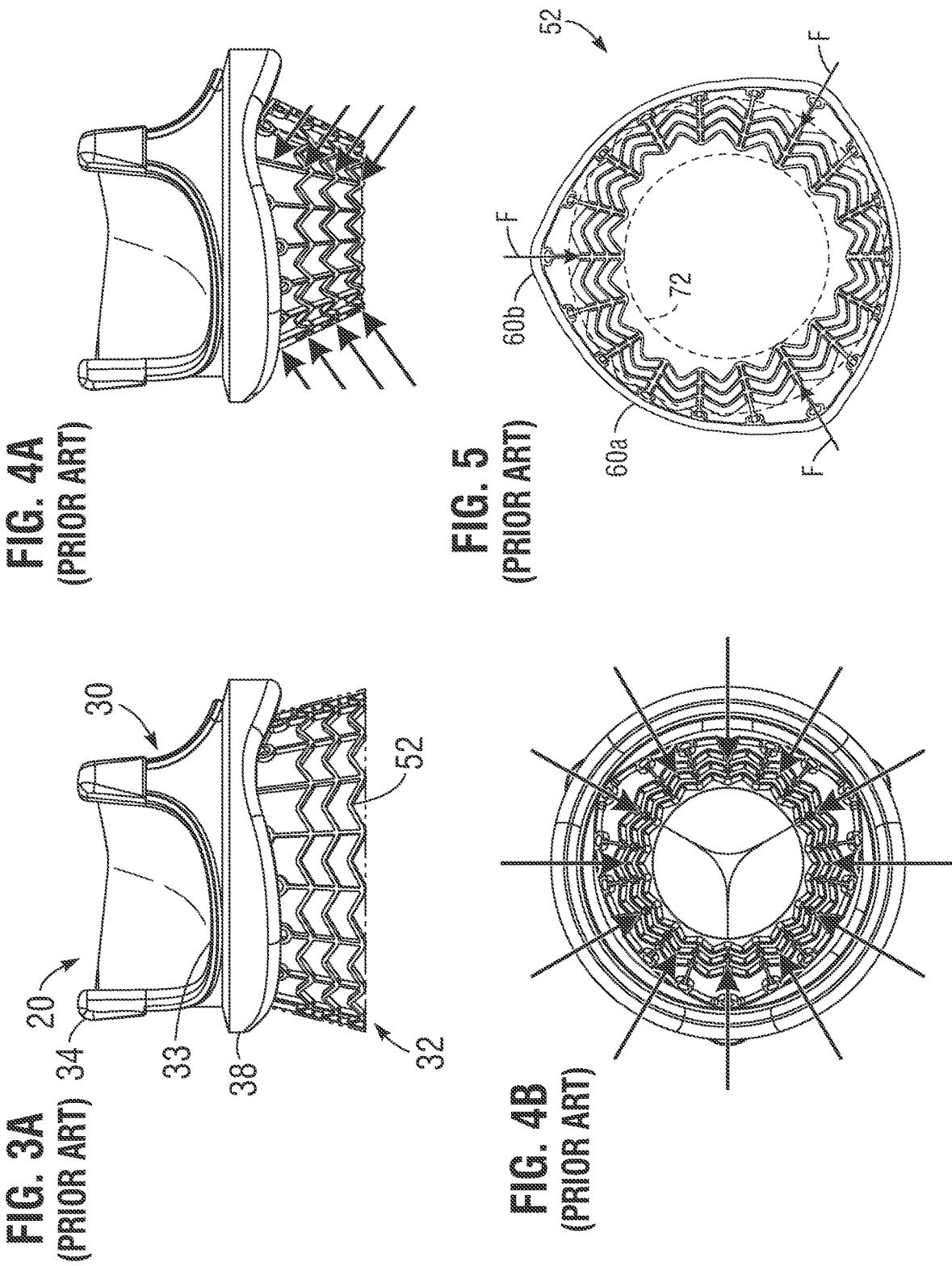
FIG. 3A is an elevational view of an assembled prior art prosthetic heart valve with an expandable skirt attached to a valve component.
FIGS. 4A and 4B are views of the prior art prosthetic heart valve schematically showing methods for crimping the expandable skirt into a conical delivery configuration after attachment to a valve member.
FIG. 5 shows the prior art expandable skirt from a lower or inflow end after a second crimping step to create a tri-lobular inflow opening.

With reference to FIG. 2A, following manufacture, the constricted stent frame 52 of the anchoring skirt 32 has an initial shape in a tapered configuration with a lower (inflow/leading) end 64 defining a smaller diameter orifice than that described by the upper (outflow/trailing) end 62. As mentioned, the anchoring skirt 32 attaches to an inflow end of the valve member 30, typically via sutures through the upper end 62 of the stent frame 52 connected to fabric on the valve member 30 or sewing ring 38. The particular sewing ring 38 as shown in FIG. 3A includes an undulating inflow contour that dips down, or in the inflow direction, in the regions of the valve cusps 33, and arcs up, in the outflow direction, in the regions of the valve commissures 34. This undulating shape generally follows the inflow end of the heart valve member wireform 50 (see FIG. 2), which seats down within the sewing ring 38. The scalloped upper end 62 of the stent frame 52 also conforms to this undulating shape, with peaks 60b aligned with the valve commissures 34 and valleys 60a aligned with the valve cusps 33.

The mid-section of the frame 52 has three rows of expandable struts 66 in a sawtooth pattern between axially-extending struts 68. The axially-extending struts 68 are in-phase with the peaks 60b and troughs 60a of the upper end 62 of the stent. The reinforcing ring defined by the thicker wire upper end 62 is continuous around its periphery and has a substantially constant thickness or wire diameter interrupted by eyelets 70, which may be used for attaching sutures between the valve member 30 and skirt 32. Note that the attachment sutures ensure that the peaks of the upper end 62 of the skirt 32 fit closely to the troughs of the sewing ring 38, which are located under the commissures of the valve.

The minimum diameter d of the upper end 62 of the covered skirt 32 will always be bigger than the ID (which defines the valve orifice and corresponding labeled valve size) defined by the prosthetic valve member 30 to which it attaches. For instance, if the upper end 62 secures to the underside of the sewing ring 38, which surrounds the support structure of the valve, it will by definition be equal to or larger than the ID or flow orifice of the support structure.

FIG. 2B illustrates the stent frame 52 isolated and in its expanded configuration. The lower end 64 has a diameter D which is larger than the diameter of the upper end 62. The expanded shape of the stent 52 is also preferably slightly flared outward toward its lower end, as shown, by virtue of expanding with a spherical balloon. This shape helps the stent conform to the contours of the left ventricle, below the aortic valve, and thus helps anchor the valve in place.

FIGS. 3A and 4A illustrate an exemplary prosthetic heart valve 20 both assembled and with a conical anchoring skirt 32 exploded from the valve component 30 and in its expanded state. Note that the anchoring skirt 32 may be wholly conical in both its contracted and expanded configurations.

In a preferred assembly sequence, the stent frame 52 is crimped into the contracted configuration prior to covering with fabric to form the anchoring skirt 32, and prior to attaching to the valve member 30. That is, a purely conical shape or the tubular-conical configuration of FIG. 2A are formed by bending the stent frame 52 in a crimping device (not shown). The cloth-covered stent frame 52 may be tubular when attached to the valve member 30, and then crimped into the conical shape shown in FIGS. 4A and 4B in a first crimping step (shown without the cloth cover). Preferably, a distributed inward crimping force is applied at even locations around the stent frame 52, such as indicated by the arrows in the figures. The frame 52 is fixed along and thus pivots inward about its scalloped upper end 62. The crimping forces are applied starting at about the level of the valleys or troughs 60a of the uneven upper end 62, as schematically indicated in FIG. 4A, leaving a short axial distance where the stent frame 52 remains cylindrical, as shown in FIG. 2A.

In an optional second crimping step, inward forces are applied unevenly to curl the lower or distal end of the stent frame 52 inward, resulting in a somewhat spherical distal end. To avoid causing overlap between the struts of the plastically-expandable stent frame 52, the forces are desirably applied to a greater extent at three locations distributed about 120° apart so that a bottom plan view in FIG. 5 shows the lower end having a trilobular shape rather than circular. More particularly, the frame 52 is desirably crimped inward more at the three regions aligned below the three commissures 34 of the valve member 30. This helps reduce the leading end profile of the valve without compromising the ability of the stent frame 52 to freely expand into the shape in FIG. 3A. The trilobular shape of the frame 52 also matches the convex-concave periphery of the aortic annulus.

Regardless of the crimping method, an orifice 72 as seen in FIG. 5 remains through the crimped stent frame 52. The orifice 72 has a sufficient diameter to enable passage of a delivery adapter termed a parting sleeve which is used to handle the prosthetic heart valve 20, as will be described below.

With the exemplary hybrid prosthetic heart valve 20 having bioprosthetic leaflets 36, the heart valve is stored prior to use in a sterile jar, typically filled with a preservative solution such as glutaraldehyde, though the valve may be a dry type. The surgeon and/or surgical staff prepares the heart valve 20 for implant by removing it from the jar and attaching it to a delivery system, such as shown above in FIG. 1. In the Edwards Intuity valve system, mentioned above, the heart valve 20 resides in the jar in a manner which facilitates attachment to the delivery system, as will be explained.

Figures 6, 7:
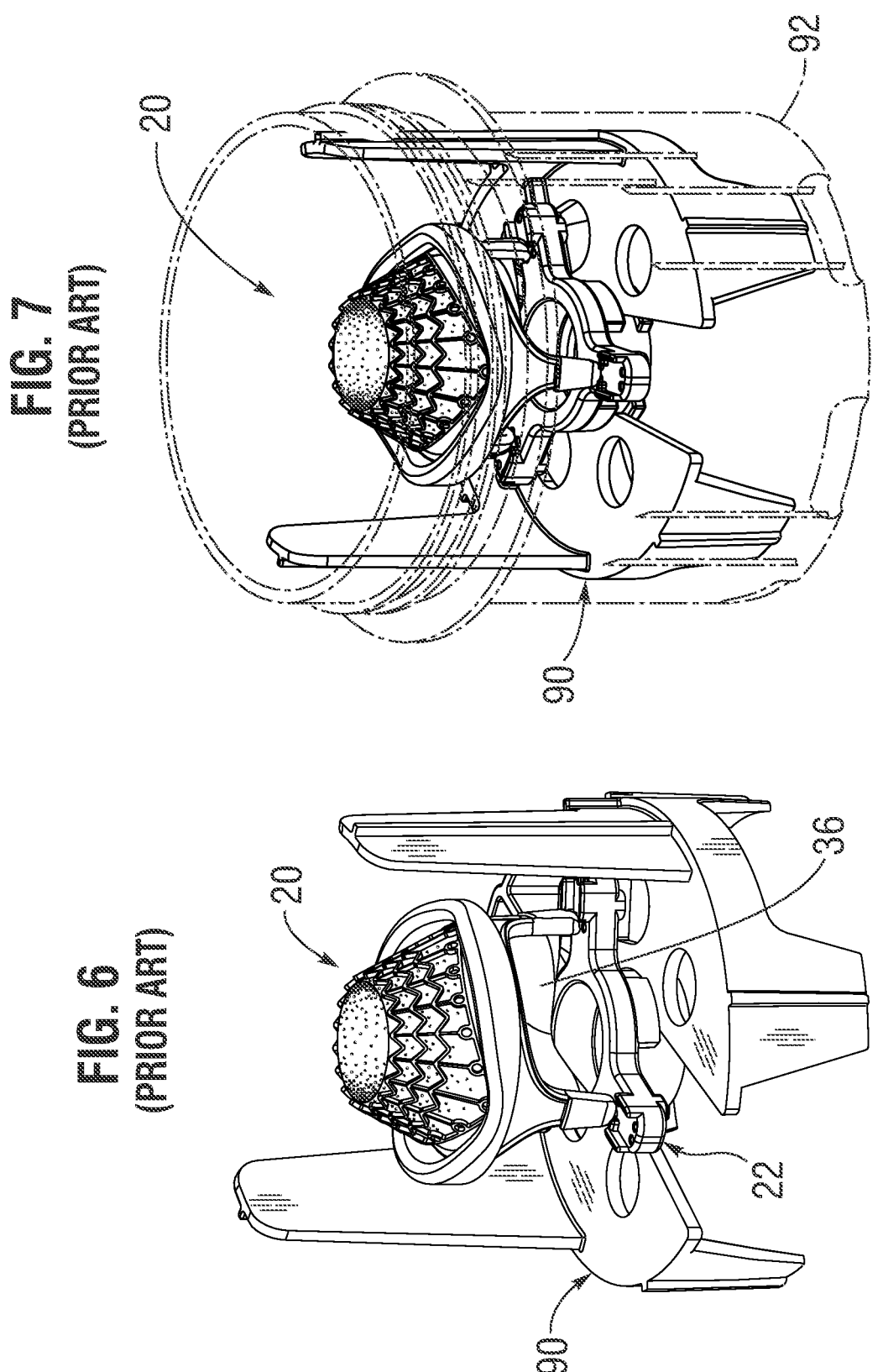
FIG. 6 is a perspective view of an assembly of a prior art prosthetic heart valve attached to a holder and positioned within a packaging sleeve.
FIG. 7 is a perspective view of the assembly of FIG. 6 positioned within a storage and shipping jar (without a lid) shown in phantom.

FIGS. 6 and 7 are perspectives of an assembly of a hybrid prosthetic heart valve 20 attached to a holder 22 and mounted to a packaging sleeve 90, which is positioned within a storage and shipping jar 92 (without a lid) in phantom. The packaging sleeve 90 provides a number of significant benefits particularly useful for the hybrid prosthetic heart valve 20 disclosed. In an exemplary embodiment, packaging sleeve 90 is a single, unitary component, preferably molded plastic. Further details of an exemplary packaging sleeve 90 are shown and described in U.S. Pat. No. 8,869,982, filed Dec. 15, 2010, the contents of which are expressly incorporated herein.

The valve holder 22 assembles to the outflow end of the valve 20, and the assembly of the valve and holder is positioned within the jar 92. To remove the heart valve 20, a user extends a shaft through the middle of the valve from the inflow end to the outflow end, couples the shaft to the valve holder 22, and removes the assembly of the valve and holder from the jar using the shaft. This is done to avoid touching the valve 20. Because the bioprosthetic leaflets 36 have free edges that project toward the outflow direction, the holder 22 is oriented toward the bottom of the jar 92 (below the valve) such that the removal shaft may pass through and part the leaflets without damage thereto.

Figures 8A, 8B, 8C:
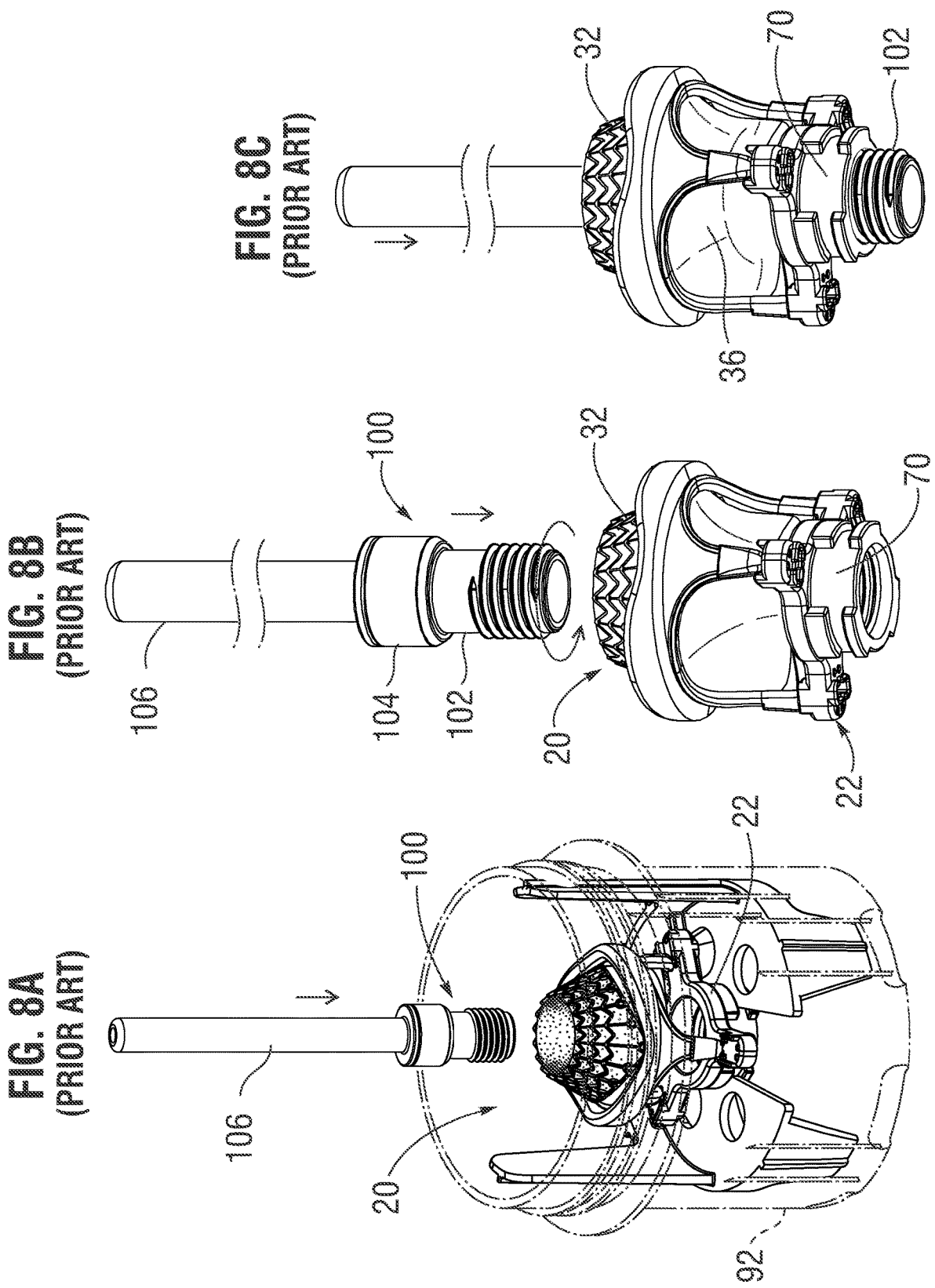
FIGS. 8A-8C shows several steps in a prior art process for coupling a leaflet parting member to a heart valve holder braced by the packaging sleeve within the storage and shipping jar.
Figures 9A, 9B, 9C:
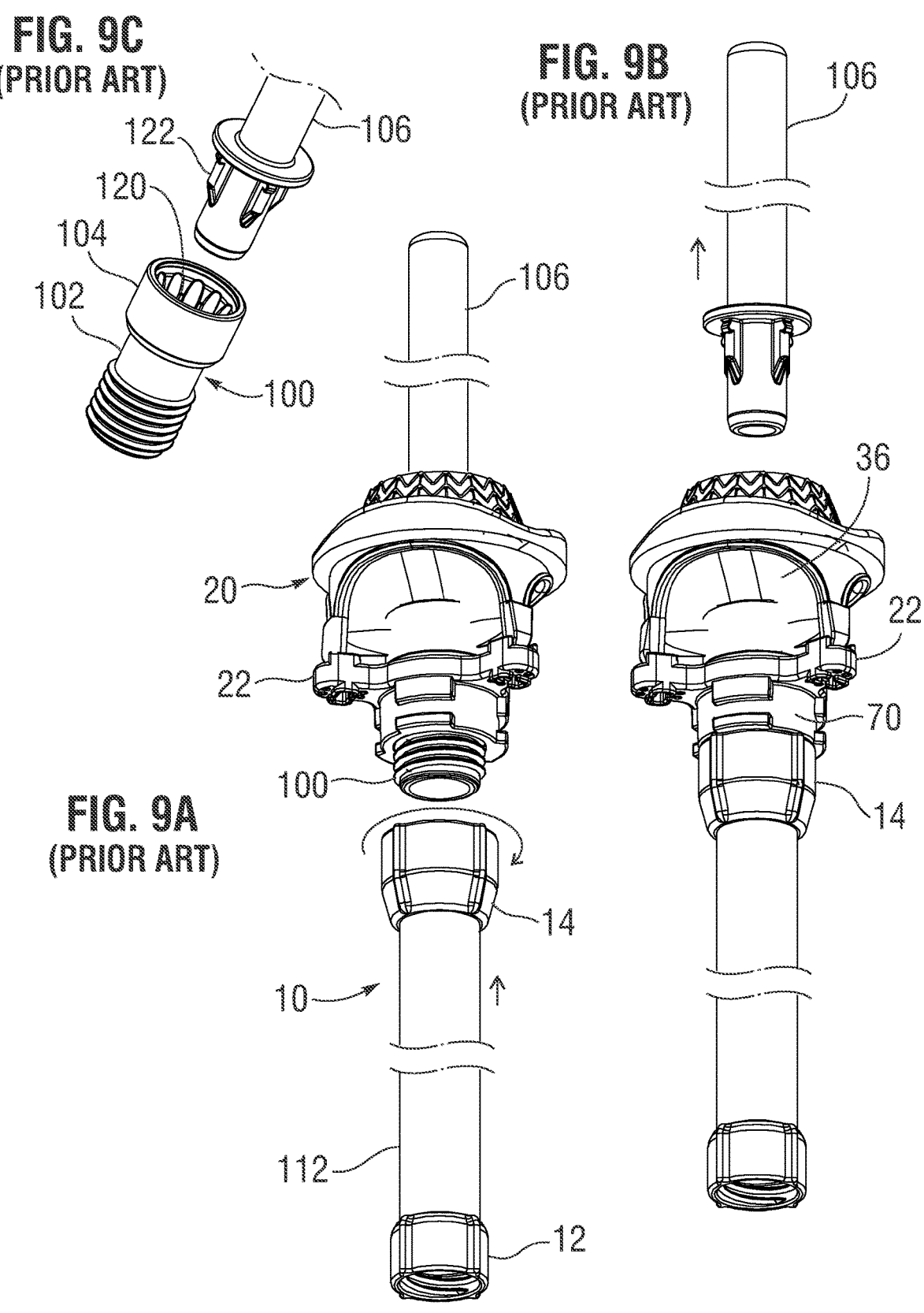
FIGS. 9A and 9B illustrate prior art steps in coupling a valve delivery tube to the leaflet parting member and removal of a handle thereof.
FIG. 9C is a detail of the leaflet parting member exploded from an elongated shaft for temporary handling.

FIGS. 8A-8C show several steps in a process for coupling a leaflet parting member 100 of a valve delivery system to the holder 22. The parting member 100 comprises a short tubular member having a stepped diameter with an externally-threaded narrower distal portion 102 and a wider proximal portion 104 with no threads. The parting member 100 couples to an elongated shaft 106 via mating threading, a snap lock, bayonet lock, a simple interference fit, or other quick-release coupling (an exemplary configuration is seen in FIG. 9C).

As depicted in FIG. 8A, the elongated shaft 106 has sufficient length to deliver the parting member 100 on its distal end into the jar 92 and through the valve 20 to the holder 22. FIGS. 8B and 8C illustrate the coupling operation with the sleeve 90 and jar 92 removed for clarity. It should be understood that although the parting member 100 is desirably coupled to the holder 22 while it remains in the jar 92, the entire assembly of the packaging sleeve 90 and valve/holder may be first removed from the jar 92 by hand or forceps. However, the reader can assume that the steps shown in FIGS. 8B and 8C are performed with the assembly still in the jar 92.

A technician advances the parting member 100 on the end of the shaft 106 through the conical anchoring skirt 32 and within the valve member 30. Since the valve leaflets 36 are angled inward from the inflow to the outflow direction (downward in the drawings), the parting member 100 easily passes therebetween in the same direction, in the process displacing the leaflets outward. Ultimately, the technician advances the parting member 100 far enough into contact with the holder 22, and screws the external threads on the distal portion 102 into the internal threads thereon.

The final position of the parting member 100 coupled to the holder 22 is shown in FIG. 8C. Note the valve leaflets 36 outwardly displaced by the proximal portion 104 of the parting member 100. The primary purpose of the parting member 100 is to open the leaflets 36 and provide a throughbore for passage of an expander, such as a balloon on the end of a catheter, for expanding the anchoring skirt 32. Without the parting member 100, attempted passage of a balloon catheter, for instance, in the direction opposite to that which the leaflets 36 extend my damage the leaflets.

Is important also to note that parting member 100 desirably couples to the holder 22 and displaces the leaflets 36 outward just before an implant procedure, typically in the operating theater. Although the parting member 100 could be pre-assembled to the holder 22 and stored and shipped with the valve/holder assembly in the jar 92, this is not advisable. Desirably, the bioprosthetic leaflets 36 remain in their closed or coapted position during what sometimes can be a very lengthy storage duration. In this way, the tissues of the leaflets 36 remain relaxed in the valve closed position, which is believed to enhance performance after implantation. Any deformation of the leaflets from long-term storage in an open position could result in regurgitation or other problems. Coupling the parting member 100 with the holder 22 during storage duration might detrimentally deform the leaflets and affect the valve performance.

As mentioned, the parting member 100 couples to the holder 22 while in the jar 92. FIGS. 9A-9C illustrate a subsequent procedure for removal of the heart valve/holder combination from the packaging sleeve 90, using the parting member 100 and attached shaft 106. First, the technician removes the entire assembly from within the jar 92, as seen in FIG. 9A. It should be noted that the valve member 30 remains surrounded and thus protected by elements of the packaging sleeve 90. Moreover, the elongated shaft 106 enables the technician to manipulate the assembly remotely without having to resort to grasping the packaging sleeve 90 with fingers or forceps, for example.

At this stage, the technician may detach the valve/holder assembly from the packaging sleeve 90 and attach a second component of the valve delivery system. The assembly of the valve 20, holder 22, parting member 100 and shaft 106 can be seen in FIG. 9A.

FIGS. 9A and 9B show the valve delivery handle 10 being coupled to the leaflet parting member 100, and subsequent removal of the elongated shaft 106. The delivery handle 10 comprises an elongated hollow shaft having the proximal coupler 14 and distal coupler 12. The distal coupler 12 includes internal threads that mate with the external threads on the narrower portion 102 of the leaflet parting member 100, as shown in FIG. 9C. The distal coupler 12 threads onto the narrower portion 102 until it abuts the proximal end of the valve holder 22. Subsequently, the elongated shaft 106 may be removed from the distal end of the parting member 100, as seen in FIG. 9B. Again, this can be accomplished through mating threading, a bayonet lock, etc., though in the illustrated embodiment the shaft 106 is simply pulled straight off of the parting member 100. More particularly, the wider proximal portion 104 of the parting member 100 provides a series of axial grooves 120 which receive axial ribs 122 on the shaft 106. The ribs 120 fit snugly in the axial grooves 124 in an interference fit, and transfer torque between the two elements.

Ultimately, the valve delivery handle 10 provides a convenient handle for manipulating the prosthetic valve 20 on its holder 22. Note that the leaflet parting member 100 remains in place displacing the leaflets 36 outward. Although not shown, the inner diameter of the hollow handle 10 desirably matches the inner diameter of the parting member 100 to provide a continuous and substantially uninterrupted throughbore from the proximal coupler 14 through the parting member, and distally beyond the leaflets 36. This continuous throughbore facilitates passage of an expander, such as a balloon on the end of a catheter, through the valve leaflets 36 to a position within the anchoring skirt 32.

As seen in FIG. 1, the assembly of the valve delivery handle 10 and prosthetic valve 20 on its holder 22 is advanced into implant position with the anchoring skirt 32 on the leading end. Although the anchoring skirt 32 is conically crimped down on its inflow (down) end, sometimes the diameter at the end closest to the valve 20 is too large and the surgeon has difficulty implanting the valve. This arises when the valve sizer used to assess the native valve orifice does not accurately reflect the size and geometry of the hybrid prosthetic valve 20, and specifically, the dimensions of the sub-annular component of the valve, e.g., the anchoring skirt 32. This sizing discrepancy sometimes means that the maximum crimped diameter of the anchoring skirt 32 is ~1.5 mm larger than the nominal size of the native valve as measured by the sizer.

Consequently, the present application contemplates a modification to the implantation procedure of the hybrid valve which provides a simple profile reduction tool for the user to perform a quick dimensional adjustment of the crimped anchoring skirt 32. This ensures that the valve is compatible with existing valve sizers, therefore reducing the issues that result in challenging implantation or implantation failures of the valve.

Figures 10A, 10B, 11A, 11B:
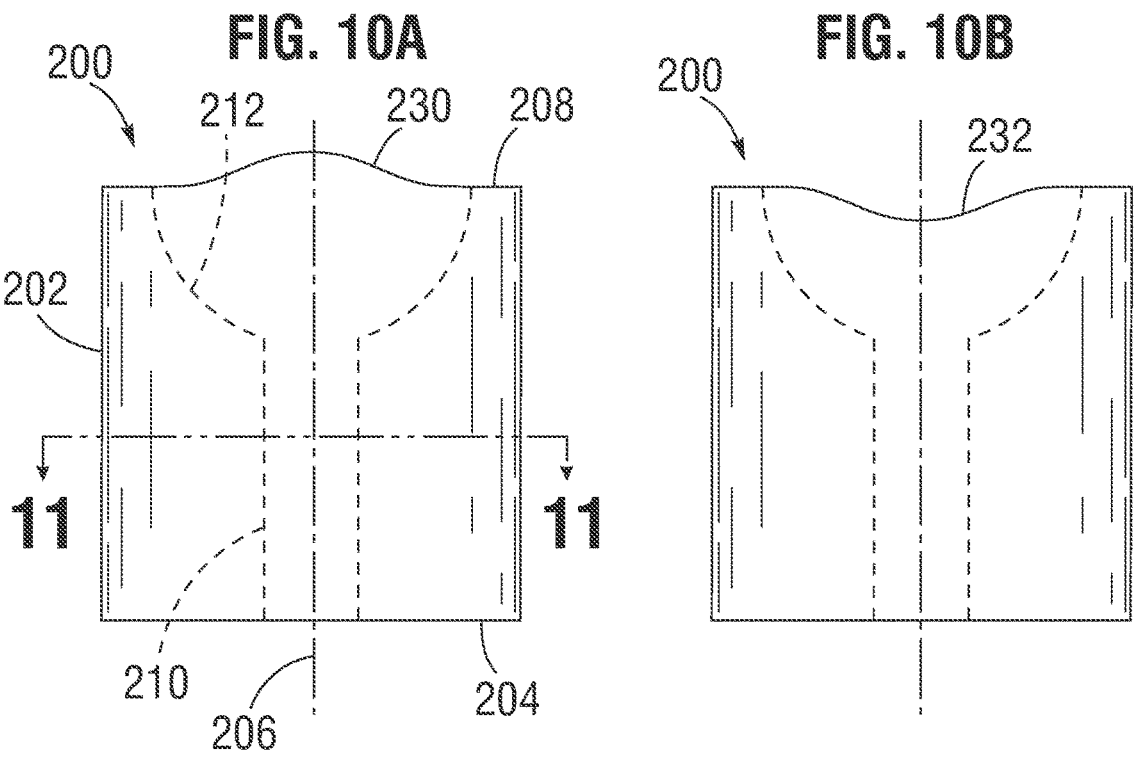
FIGS. 10A and 10B are elevational views of an exemplary crimping die that is used to compress an inlet end of an expandable skirt of a hybrid prosthetic heart valve after removal from a storage jar just prior to implantation.
FIGS. 11A and 11B are alternative lateral sectional views of crimping dies.

FIGS. 10A and 10B are elevational views of an exemplary crimping die 200 that is used to compress an inlet end of an expandable skirt 32 of a hybrid prosthetic heart valve 20 after removal from a storage jar and just prior to implantation, and FIGS. 11A and 11B are alternative sectional views of the crimping die. The profile adjustment crimping die 200 eliminates the potential size discrepancy between valve and annulus sizer with a simple step performed during the valve implantation process. Prosthetic heart valves are typically provided in odd mm sizes between 19-29 mm in 2 mm increments. For example: If the nominal size of the valve is 19 mm with an actual maximum crimped frame diameter of about 20.5 mm, after using the profile adjustment tool the maximum diameter of the frame would now be about 19 mm or less. Preferably, the maximum diameter of the expandable skirt 32 is reduced by at least about 1.5 mm. With this size discrepancy eliminated, some of the present implantation difficulties that are being experienced would be significantly minimized or eliminated, including difficulty seating the valve, valve pop up, valve displacement while tying sutures, and improper valve position after tying sutures.

The illustrated crimping die 200 comprises a single piece monolithic body 202 which may be cylindrical or otherwise. A bottom end 204 is relatively flat and perpendicular to a longitudinal axis 206, while an upper end 208 undulates axially. An axial throughbore from upper end 208 to lower end 204 includes a narrow lower bore 210 and a wider upper cavity 212. The narrow lower bore 210 is preferably circular and constant in cross-section, while the wider upper cavity 212 may be hemispherical or conical, or a combination thereof, becoming wider towards the upper end 208. In one specific embodiment, the upper cavity 212 is generally hemispherical but has a trilobular shape so as to impart a radial size reduction greater in three evenly spaced regions, which is the way the anchoring skirt 32 is crimped during manufacture.

FIG. 11B shows a version which includes external ribs 220 added to the cylindrical outer profile to prevent the crimping die 200 from rolling if placed on its side. Of course, the external shape could be formed to be rectangular or other non-circular circumferential shape, or to have one or more flat areas, outer ribs, and/or bumps other than those shown to prevent rolling.

Figure 12:
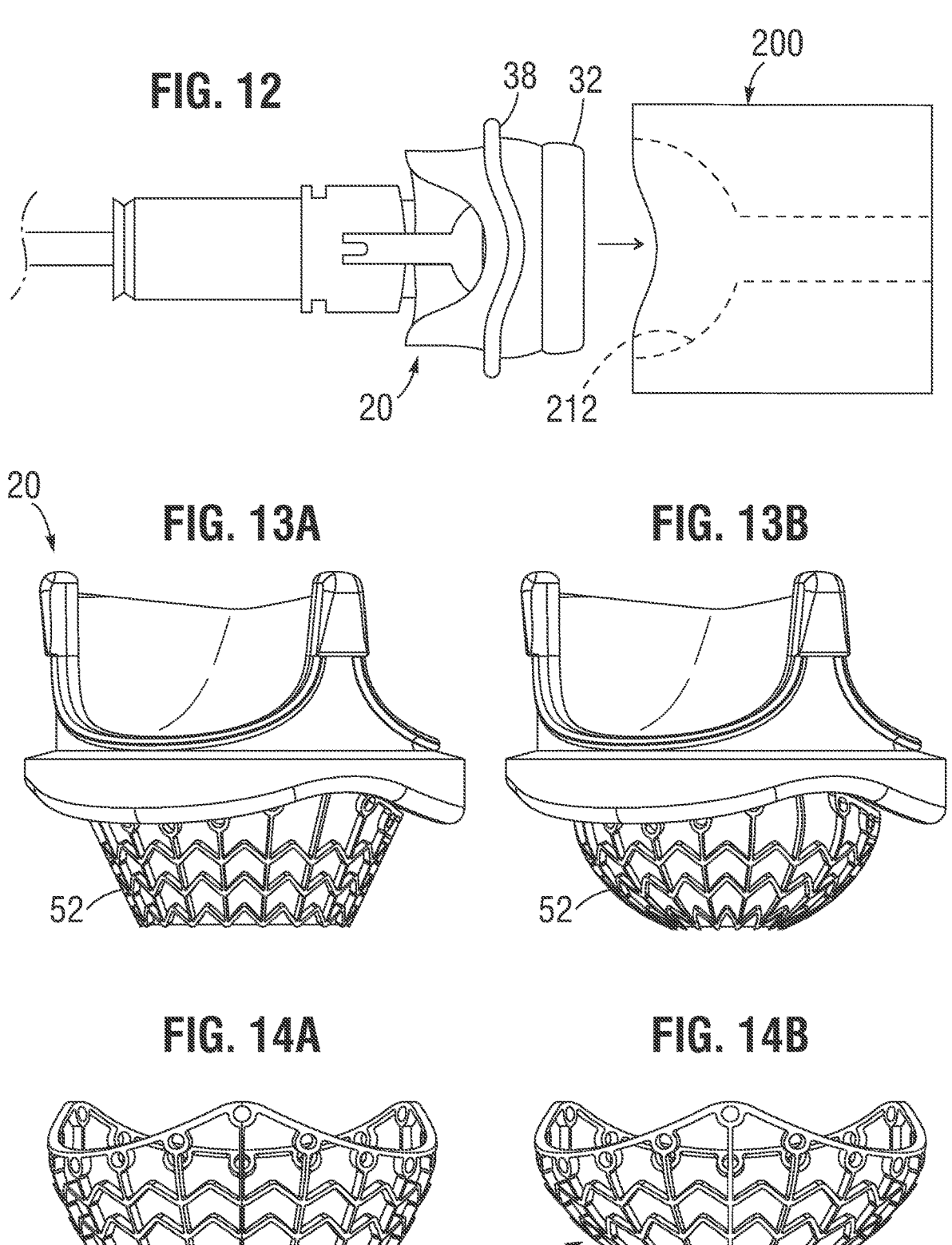
FIG. 12 is a side view showing advancement of a hybrid prosthetic heart valve on the distal end of a delivery system toward the exemplary crimping die.

FIG. 12 is a side view showing advancement of a hybrid prosthetic heart valve 20 on the distal end of a delivery system, such as including the delivery handle 10, toward the exemplary crimping die 200. The user gently pushes the leading end of the anchoring skirt 32 into the wider upper cavity 212 of the crimping die 200 and applies enough force to further crimp the inner stent frame 52 of the skirt. The upper cavity 212 is sufficiently shallow and shaped to crimp the inner stent frame 52 down from the shapes shown in FIGS. 13A and 14A to those shown in FIGS. 13B and 14B. That is, the inner stent frame 52 is reshaped from approximately conical to approximately hemispherical. FIGS. 13A and 13B show the hybrid prosthetic heart valve 20 before and after compression of the expandable skirt using the crimping die 200, and FIGS. 14A and 14B show just the inner stent frame 52 of the expandable skirt before and after compression. For example, if the nominal size of the valve 20 is 19 mm, the maximum diameter of the anchoring skirt 32 should be about 19 mm or less, which would accurately reflect the 19 mm sizer.

To ensure the appropriate crimp is applied, the upper cavity 212 may be shaped (see FIG. 17) so that the proper crimp is applied when the sealing ring 38 that circumscribes the valve 20 contacts the upper end 208 of the crimping die 200 surrounding the upper cavity 212. In situations where the sealing ring 38 axially undulates around its periphery, as described above, the upper end 208 of the crimping die 200 also undulates, with peaks 230 and valleys 232 as seen in FIGS. 10A and 10B. This matching shape between the upper end 208 and the sealing ring 38 ensures complete insertion of the expandable skirt 32 into the crimping cavity 212 of the die 200. The undulating shapes of the upper end 208 and sealing ring 38 also cooperate so that the user can axially rotate the valve 20 to fully seat the anchoring skirt 32 within the upper shaping cavity 212.

It should be understood that the extra crimp applied by the user with the crimping die 200 must be done after removal of the valve 20 from the storage jar 92 and prior to delivery. This is because the anchoring skirt 32 of the stored valve must possess an orifice diameter at its inflow end sufficient to permit passage of the parting sleeve 100, as seen in FIG. 8A. Once the valve 20 is removed from the storage jar 92, by first attaching the parting sleeve 100, and assembled with the delivery system, as seen in FIG. 9B, the orifice diameter at the inflow end of the anchoring skirt 32 need only be large enough to permit passage of the leading tip of a constricted balloon catheter used to expand the skirt, a diameter that is significantly smaller than that needed for passage of the parting sleeve 100. Indeed, the constricted balloon catheter passes through the lumen of the parting sleeve 100 as it is advanced through the valve 20.

One potential issue with operation of the crimping die 200 is that the user may not adequately perform the reduction of the crimped frame maximum diameter with the tool, and without a physical check there is no way to confirm that this procedural step has been correctly performed. Consequently, a measuring gauge incorporated into the crimping die and described below is proposed.

Figures 15A, 15B, 16, 17:
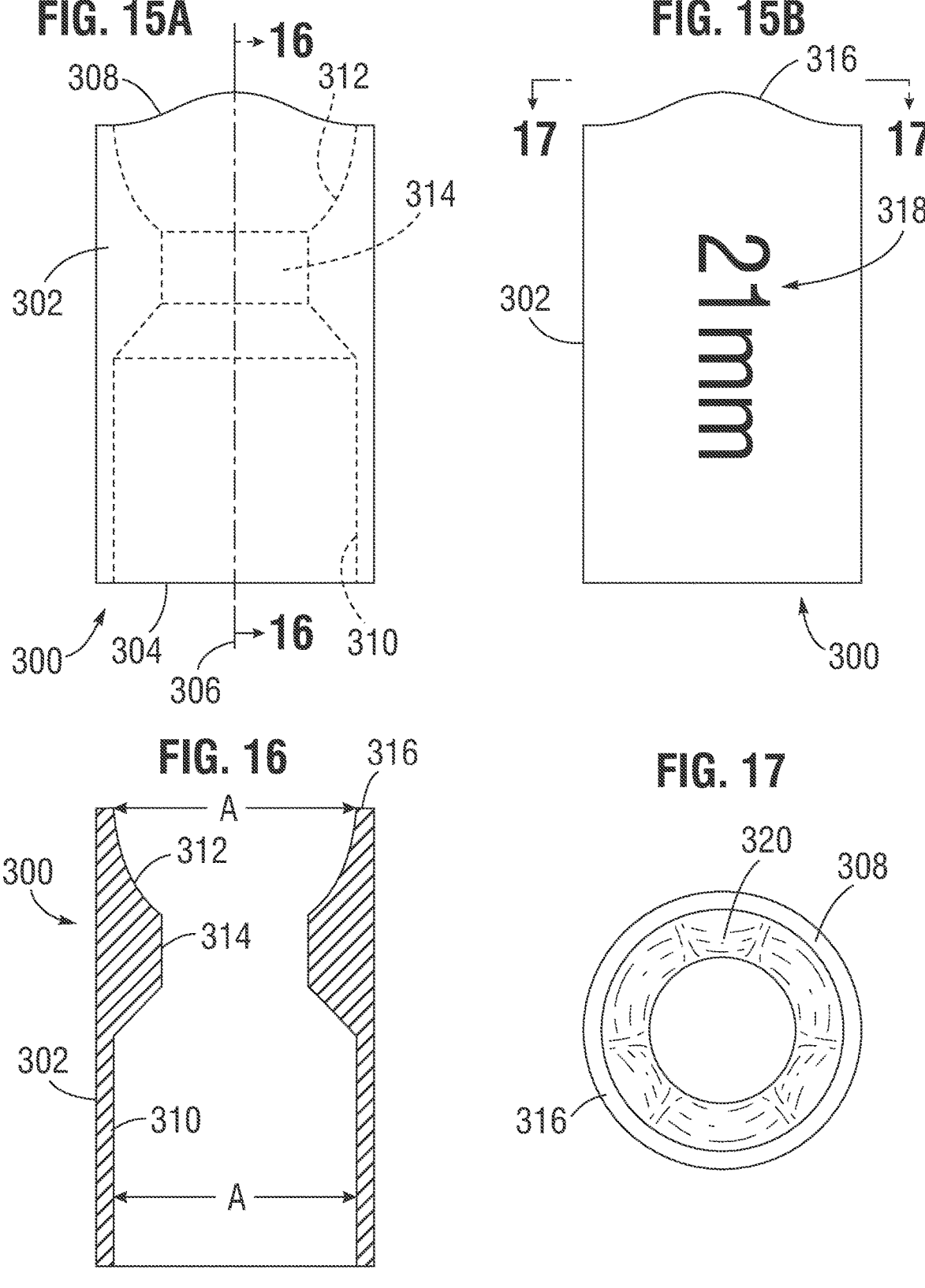
FIGS. 15A and 15B are elevational views of an alternative crimping die for compressing an expandable skirt of a hybrid prosthetic heart valve.
FIG. 16 is a longitudinal sectional view of the crimping die of FIGS. 15A and 15B.
FIG. 17 is a top plan view of the alternative crimping die showing an exemplary crimping cavity.

FIGS. 15A and 15B are elevational views of an alternative crimping and measuring die 300 that is used to compress an expandable skirt 32 of a hybrid prosthetic heart valve 20 after removal from a storage jar and just prior to implantation.

The illustrated crimping die 300 comprises a monolithic body 302 which may be cylindrical or otherwise. A bottom end 304 is relatively flat and perpendicular to a longitudinal axis 306, while an upper end 308 undulates axially around its periphery. An axial throughbore from upper end 308 to lower end 304 includes a lower cavity 310 and an upper cavity 312 joined by an intermediate passage 314. The lower cavity 310 is preferably circular and constant in cross-section, while the wider upper cavity 312 may be hemi-spherical or conical, or a combination thereof, becoming wider towards the upper end 308. The upper end 308 of the crimping die 300 desirably undulates, with peaks 316 at three locations 120° apart and valleys in between. This shape matches an undulating sealing ring of a prosthetic heart, as explained above.

FIG. 15B also shows a size indicator 318 engraved, embossed or imprinted on an exterior surface of the crimp-ing die 300. As explained, prosthetic heart valves are often provided and labeled in sizes of 19-21-23-25-27-29 mm, which translates to the diameter of the orifice of the heart valve. Heart valve sizers are also similarly sized and labeled. Consequently, the crimping dies described herein are pref-erably also labeled for the size of the heart valve that they are intended to service.

FIG. 16 is a longitudinal sectional view of the crimping die of FIGS. 15A and 15B, and shows the various inner surfaces 310, 312, 314. As will be shown, the upper cavity 312 has a somewhat hemispherical shape and is designed to crimp an inner stent frame 52 of an anchoring skirt 32 of a hybrid heart valve. An upper diameter A of the upper cavity 312 preferably matches a diameter A of the cylindrical lower cavity 310. The lower cavity 310 serves as a gauge to measure the size of the anchoring skirt 32 once it has been crimped in the upper cavity 312.

In one specific embodiment, as seen in FIG. 17, the upper cavity 312 is generally hemispherical but has a trilobular shape so as to impart a radial size reduction greater in three evenly spaced regions around the anchoring skirt 32, which is the way the anchoring skirt is crimped during manufac-ture. More specifically, the upper cavity 312 has three regions 320 that are generally convex (bowed inward) and spaced 120° apart and align with the three peaks 316 on the upper end 308. In between the three convex regions 320, the upper cavity 312 is generally concave and hemispherical. The three convex regions 320 do not commence at the top of the cavity 312, but instead start a short distance (e.g., about 2-3 mm) below the upper end 308 to accommodate a short axial length of the stent frame 52 of the anchoring skirt 32 that is circular in radial section, as seen in FIG. 14B.

Figures 18A, 18B:
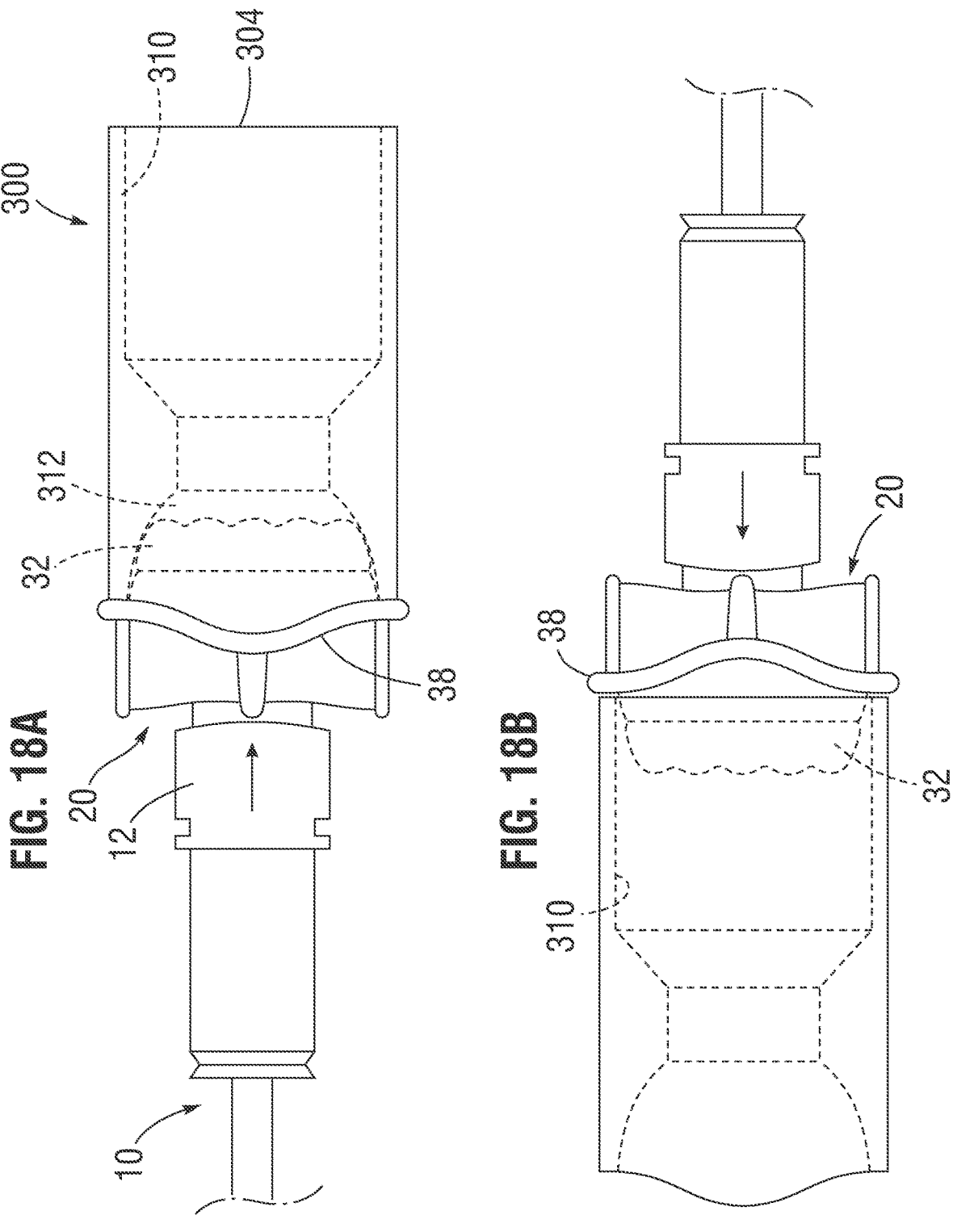
FIGS. 18A and 18B are side views showing advancement of a hybrid prosthetic heart valve on the distal end of a delivery system into both ends of the alternative crimping die FIGS. 15A and 15B.

FIGS. 18A and 18B are side views showing advancement of a hybrid prosthetic heart valve 20 on the distal end of a delivery system handle 10 into both ends of the alternative crimping die FIGS. 15A and 15B.

The user gently pushes the leading end of the anchoring skirt 32 into the wider upper cavity 312 of the crimping die 300 and applies enough force to further crimp the inner stent frame 52 of the skirt. The upper cavity 312 is sufficiently shallow and shaped to crimp the inner stent frame 52 down from the shapes shown in FIGS. 13A and 14A to those shown in FIGS. 13B and 14B. That is, the inner stent frame 52 is reshaped from approximately conical to approximately hemispherical. FIGS. 13A and 13B show the hybrid pros-thetic heart valve 20 before and after compression of the expandable skirt using the crimping die 300, and FIGS. 14A and 14B show just the inner stent frame 52 of the expandable skirt before and after compression. For example, if the nominal size of the valve 20 is 19 mm, the maximum diameter of the crimped anchoring skirt 32 should be about 19 mm or less, which would accurately reflect the 19 mm sizer.

To ensure complete crimping, the upper cavity 312 may be shaped so that the proper crimp is applied when the sealing ring 38 that circumscribes the valve 20 contacts the upper end 308 of the crimping die 300 surrounding the upper cavity 312. In situations where the sealing ring 38 axially undulates around its periphery, as described above, the upper end 308 of the crimping die 300 also undulates, with peaks 316 and valleys in between, as seen in FIGS. 15B and 17.

Once the user has pressed the heart valve 20, and more particular the anchoring skirt 32, into the shaping cavity 312, the valve is withdrawn. At this point, the user inserts the heart valve 20 anchoring skirt 32 first into the opposite gauge end of the crimping die 300 having the cylindrical cavity 310. As explained above, the cylindrical cavity 310 has a diameter A that matches the largest diameter of the shaping cavity 312. If the anchoring skirt 32 fits completely within the measuring cavity 310, the user is apprised that a proper crimp has been applied. On the other hand, if the anchoring skirt 32 does not fit fully into the measuring cavity 310, the crimping operation can be repeated in the shaping cavity 312. This ensures that a full crimp is applied to the anchoring skirt 32 so that it will fit into the previously sized native heart valve annulus, and eliminates any uncertainty therefore. Although the bottom end 304 is shown flat, it also may have an undulating periphery like the top end 308 to match the contours of the sealing ring 38.

While the invention has been described in its preferred embodiments, it is to be understood that the words which have been used are words of description and not of limita-tion. Therefore, changes may be made within the appended claims without departing from the true scope of the inven-tion.

What is claimed is:

1. A method of implantation of a hybrid prosthetic aortic heart valve, comprising:

procuring a hybrid prosthetic aortic heart valve having a non-expandable, non-collapsible valve member and a generally tubular plastically-expandable anchoring skirt attached to and projecting in an inflow direction from the valve member, the anchoring skirt having an initial shape that decreases in radial dimension from an outflow end connected to the valve member and defin-ing a first diameter orifice to a free inflow end having a second diameter orifice, the heart valve being stored in a sterile storage jar and attached to a valve holder projecting in an outflow direction;

passing a parting sleeve through the anchoring skirt and valve member and attaching the parting sleeve to the valve holder;

removing the heart valve attached to the valve holder from the storage jar, then performing at least the following steps;

advancing the anchoring skirt into a crimping die to crimp the anchoring skirt and reduce both the first and second diameter orifices;

delivering the heart valve anchoring skirt first to a native aortic heart valve annulus; and plastically-expanding the anchoring skirt to contact the native aortic heart valve annulus.

2. The method of claim 1, wherein the crimping die comprises a body with a throughbore along a longitudinal axis and an enlarged crimping cavity opening at a first longitudinal end of the body, the method including pushing the heart valve anchoring skirt first into the crimping cavity.

3. The method of claim 2, wherein the heart valve has a sealing ring surrounding a junction between the valve member and anchoring skirt, and the method includes advancing the heart valve anchoring skirt first into the crimping cavity until the sealing ring contacts the first longitudinal end of the body.

4. The method of claim 3, wherein the sealing ring has an axially undulating shape with peaks and valleys, and the first longitudinal end of the body has a matching axially undulating shape surrounding the crimping cavity.

5. The method of claim 2, wherein the crimping die body has an external shape that inhibits the body from rolling around the longitudinal axis on a support surface.

6. The method of claim 2, further including advancing the anchoring skirt into a second end of the crimping cavity to ensure that the first diameter orifice has been crimped to a desired size.

7. The method of claim 1, wherein the initial shape of the anchoring skirt is conical.

8. The method of claim 7, wherein the crimping cavity is hemispherical to crimp the anchoring skirt into a spherical curvature.

9. The method of claim 1, wherein the initial shape of the anchoring skirt is generally conical with a trilobular crimped inflow end.

10. The method of claim 9, wherein the crimping cavity is generally hemispherical with a trilobular contour that matches the shape of the anchoring skirt so as to crimp the anchoring skirt into a spherical curvature.

11. The method of claim 1, further including attaching a handling shaft to the parting sleeve to remove the heart valve from the storage jar.

12. A method of implantation of a hybrid prosthetic aortic heart valve, comprising:

procuring a hybrid prosthetic aortic heart valve having a non-expandable, non-collapsible valve member and a generally tubular plastically-expandable anchoring skirt attached to and projecting in an inflow direction from the valve member, the anchoring skirt having an outflow end connected to the valve member and defining a first diameter orifice to a free inflow end having a second diameter orifice, the heart valve being stored in a sterile storage jar and attached to a valve holder projecting in an outflow direction;

removing the heart valve from the storage jar, then performing at least the following steps;

crimping the anchoring skirt to reduce both the first and second diameter orifices;

delivering the heart valve anchoring skirt first to a native aortic heart valve annulus; and plastically-expanding the anchoring skirt to contact the native aortic heart valve annulus.

13. The method of claim 12, wherein the step of crimping includes advancing the anchoring skirt into a crimping die comprising a body with a throughbore along a longitudinal axis and an enlarged crimping cavity opening at a first longitudinal end of the body, the method including pushing the heart valve anchoring skirt first into the crimping cavity.

14. The method of claim 13, wherein the heart valve has a sealing ring surrounding a junction between the valve member and anchoring skirt, and the method includes advancing the heart valve anchoring skirt first into the crimping cavity until the sealing ring contacts the first longitudinal end of the body.

15. The method of claim 14, wherein the sealing ring has an axially undulating shape with peaks and valleys, and the first longitudinal end of the body has a matching axially undulating shape surrounding the crimping cavity.

16. The method of claim 13, wherein the crimping die body has an external shape that inhibits the body from rolling around the longitudinal axis on a support surface.

17. The method of claim 13, wherein the crimping cavity is hemispherical to crimp the inflow end of the anchoring skirt into a spherical curvature.

18. The method of claim 13, wherein the crimping cavity is on a first end, and the method further includes advancing the anchoring skirt into a second end of the crimping cavity to ensure that the first diameter orifice has been crimped to a desired size.

19. The method of claim 12, wherein the initial shape of the anchoring skirt is conical.

20. The method of claim 12, wherein the initial shape of the anchoring skirt is generally conical with a trilobular crimped inflow end.

21. The method of claim 20, wherein the step of crimping includes advancing the anchoring skirt into a crimping die, and the crimping cavity is generally hemispherical with a trilobular contour that matches the shape of the anchoring skirt so as to crimp the inflow end of the anchoring skirt into a spherical curvature.

22. The method of claim 12, further including, before the heart valve is removed from the storage jar and prior to the step of crimping, passing a parting sleeve through the anchoring skirt and valve member and attaching the parting sleeve to the valve holder, and then attaching a handling shaft to the parting sleeve and removing the heart valve from the storage jar.

* * * * *